(12) United States Patent
Zwirnmann et al.

(10) Patent No.: US 8,052,691 B2
(45) Date of Patent: Nov. 8, 2011

(54) SPRING LOADED FIXATION ELEMENT INSERTION DEVICE

(75) Inventors: Ralph Fritz Zwirnmann, Roslyn, PA (US); Michael C. Chen, King of Prussia, PA (US)

(73) Assignee: Synthes USA, LLC, West Chester, PA (US)

( * ) Notice: Subject to any disclaimer, the term of this patent is extended or adjusted under 35 U.S.C. 154(b) by 1758 days.

(21) Appl. No.: 10/992,259

(22) Filed: Nov. 18, 2004

(65) Prior Publication Data
US 2005/0070918 A1   Mar. 31, 2005

(51) Int. Cl.
*A61F 2/46* (2006.01)
(52) U.S. Cl. .................................... 606/86 R; 606/104
(58) Field of Classification Search ............... 81/463; 173/121, 120, 188, 202; 606/72, 104, 151, 606/213, 219, 86 R, 96; 227/146
See application file for complete search history.

(56) References Cited

U.S. PATENT DOCUMENTS

| | | | | |
|---|---|---|---|---|
| 1,572,046 A | * | 2/1926 | Seiler | 30/367 |
| 1,952,395 A | * | 3/1934 | Tillyer et al. | 81/10 |
| 2,212,339 A | * | 8/1940 | Cullen | 227/146 |
| 2,257,979 A | * | 10/1941 | Rubinstein | 403/289 |
| 3,010,193 A | * | 11/1961 | Croall, Jr et al. | 29/278 |
| 4,129,975 A | * | 12/1978 | Gabriel | 403/289 |
| 4,402,641 A | | 9/1983 | Arff | 411/510 |
| 4,441,563 A | * | 4/1984 | Walton, II | 173/213 |
| 4,708,209 A | * | 11/1987 | Aspinwall | 173/93 |
| 4,776,328 A | | 10/1988 | Frey et al. | 128/92 VT |
| 4,776,739 A | | 10/1988 | Hamman | 411/510 |
| 4,928,560 A | * | 5/1990 | Bang | 81/463 |
| 4,963,144 A | | 10/1990 | Huene | 606/73 |
| 5,071,420 A | | 12/1991 | Paulos et al. | 606/99 |
| 5,139,499 A | | 8/1992 | Small et al. | 606/73 |
| 5,236,431 A | | 8/1993 | Gogolewski et al. | 606/72 |
| 5,258,016 A | | 11/1993 | DiPoto et al. | 606/232 |
| 5,261,914 A | | 11/1993 | Warren | 606/73 |
| 5,268,001 A | | 12/1993 | Nicholson et al. | 606/72 |
| 5,391,170 A | | 2/1995 | McGuire et al. | 606/86 |
| 5,398,861 A | * | 3/1995 | Green | 227/175.1 |
| 5,431,660 A | * | 7/1995 | Burke | 606/104 |
| 5,445,641 A | | 8/1995 | Frigg et al. | 606/86 |
| 5,522,843 A | | 6/1996 | Zang | 606/232 |
| 5,578,057 A | | 11/1996 | Wenstrom, Jr. | 606/232 |
| 5,584,860 A | | 12/1996 | Goble et al. | 606/232 |

(Continued)

FOREIGN PATENT DOCUMENTS

DE      29 33 141      4/1980

(Continued)

*Primary Examiner* — Thomas C. Barrett
*Assistant Examiner* — Michael Araj
(74) *Attorney, Agent, or Firm* — Woodcock Washburn LLP (57) ABSTRACT

The invention relates to a device for attaching fixation elements to bone, having a longitudinal member with a channel extending therein adapted for receiving at least one fixation element. A shaft extends within the channel and is positioned coaxially within at least a portion of the longitudinal member and at least a portion of the shaft is retained within the longitudinal member and a distal end of the shaft is configured and adapted to contact at least a portion of the fixation element received within the longitudinal member. A spring is positioned adjacent the shaft for resiliently biasing the shaft in an axial direction and the shaft is moveable with respect to the longitudinal member to drive the fixation element into bone.

14 Claims, 7 Drawing Sheets

U.S. PATENT DOCUMENTS

| | | | |
|---|---|---|---|
| 5,590,574 A | 1/1997 | Lide | 81/124.1 |
| 5,672,038 A | 9/1997 | Eaton | 411/510 |
| 5,683,401 A | 11/1997 | Schmieding et al. | 606/104 |
| 5,720,766 A | 2/1998 | Zang et al. | 606/232 |
| 5,735,854 A | 4/1998 | Caron et al. | 606/73 |
| 5,741,268 A | 4/1998 | Schütz | 606/104 |
| 5,800,109 A | 9/1998 | Carruthers | 411/510 |
| 5,814,051 A | 9/1998 | Wenstrom, Jr. | 606/104 |
| 5,893,856 A | 4/1999 | Jacob et al. | 606/151 |
| 5,895,396 A | 4/1999 | Day et al. | 606/151 |
| 5,901,424 A | 5/1999 | Rector | 27/21.1 |
| 5,904,685 A | 5/1999 | Walawalkar | 606/73 |
| 5,906,624 A | 5/1999 | Wenstrom, Jr. | 606/139 |
| 6,007,539 A | 12/1999 | Kirsch et al. | 606/75 |
| 6,273,893 B1 * | 8/2001 | McAllen et al. | 606/104 |
| 6,402,759 B1 * | 6/2002 | Strong et al. | 606/104 |
| 7,147,641 B2 * | 12/2006 | Chen | 606/72 |

FOREIGN PATENT DOCUMENTS

| | | |
|---|---|---|
| EP | 0 834 281 A1 | 4/1998 |
| EP | 1 090 591 A2 | 4/2001 |
| EP | 1 090 591 A3 | 4/2001 |
| FR | 2 682 587 | 4/1993 |
| FR | 2 777 443 | 10/1999 |

* cited by examiner

SPRING LOADED FIXATION ELEMENT INSERTION DEVICE

CROSS-REFERENCE TO RELATED APPLICATIONS

Priority of U.S. patent application Ser. No. 10/287,693, filed on Nov. 5, 2002, which claims priority under 35 U.S.C. §119 to Provisional Application No. 60/330,977, filed on Nov. 5, 2001, is claimed and priority of U.S. patent application Ser. No. 09/866,841, filed on May 30, 2001 and PCT Application No. PCT/US02/16656, filed on May 28, 2002 is claimed under 35 U.S.C. §120, the entire contents of which are incorporated by reference.

FIELD OF THE INVENTION

The present invention relates to a device for the storage and dispensing of osteosynthetic fixation elements, and in particular to a device for attaching fixation elements to bone.

BACKGROUND OF INVENTION

In the surgical treatment of fractures in the maxillofacial area, as well as fractures of the foot and hand, a trend toward preferring ever-smaller implants can clearly be noted. The reason for this is the generally increased understanding of the biomechanical bases of osteosynthesis. In the field of treating maxillofacial fractures, more attention can be paid to the cosmetic results of osteosynthesis, thanks to the miniaturization of implants. In the field of hand surgery, restrictions on movement in the area of the fingers can be avoided. In this regard, smaller osteosynthetic implants in the fingers can be placed under the tendons. In the case of an implant with a large cross-section, the tendons need no longer be extended to their full length.

The dimensions of some smaller implants (screws, plates and tacks) are in the range of about 0.8 mm to about 2.0 mm. Problems in the area of packaging, storage and manipulation during surgery arise due to this miniaturization. Handling in the operating room, particularly in the maxillofacial area, has proved difficult. Depending on the degree of severity of the fracture or correction, up to 40 bone fixation elements, such as tacks or screws, may be required. These screws must be taken individually by the operating room nurse from a so-called screw rack, checked for length, placed on a screwdriver and given to the surgeon. The surgeon must, in turn, insert them through the osteosynthesis plate into pre-drilled screw holes. During the transfer of the screw and the attempted insertion of the screw, it often falls off the screwdriver, into the wound or onto the operating room floor. The attempt to find a lost screw is often excessively time-consuming, given their dimensions and extends the time spent in surgery. The frequent loss of screws in the operating room, and during packing and sterilization, causes unnecessary costs for the hospital. Thus, it is desirable to have a simple device that can be operated with one hand, thereby freeing the operator's other hand to align the fixation element or perform other tasks.

An additional problem in dealing with mini-screws arises during their implantation. After the surgeon has selected the osteosynthesis plate proper for the fracture in question, a plate is positioned over the fracture. A hole is then drilled for the screw (0.5-1.5 mm diameter) through one of the plate holes. Commonly, problems arise in controlling the amount of force applied during the insertion of the screw and or tack. For example, if a surgeon is required to insert a screw or tack with manual force, the manual force could be transmitted to the surrounding bone, which could bend thin and/or flexible bone in young patients.

Also, problems such as surgical gloves tearing or hand pinching can arise if the insertion device has parts that move externally during the firing of the device. Thus, a need exists for an insertion device that minimizes the manual force exertion required and to minimize the gross forces applied to the surrounding bone during insertion.

SUMMARY OF INVENTION

The present invention relates to a device for attaching fixation elements to bone, including a longitudinal member extending along a longitudinal axis from a proximal end to a distal end and having a channel extending therein adapted for receiving at least one fixation element. A shaft extends within the channel and is positioned coaxially within at least a portion of the longitudinal member and at least a portion of the shaft is retained within the longitudinal member and a distal end configured and adapted to contact at least a portion of the fixation element received within the longitudinal member. A spring is positioned adjacent the shaft for resiliently biasing the shaft in an axial direction and the shaft is moveable with respect to the longitudinal member to drive the fixation element into bone.

DETAILED DESCRIPTION OF THE PREFERRED EMBODIMENTS

Figure 1:
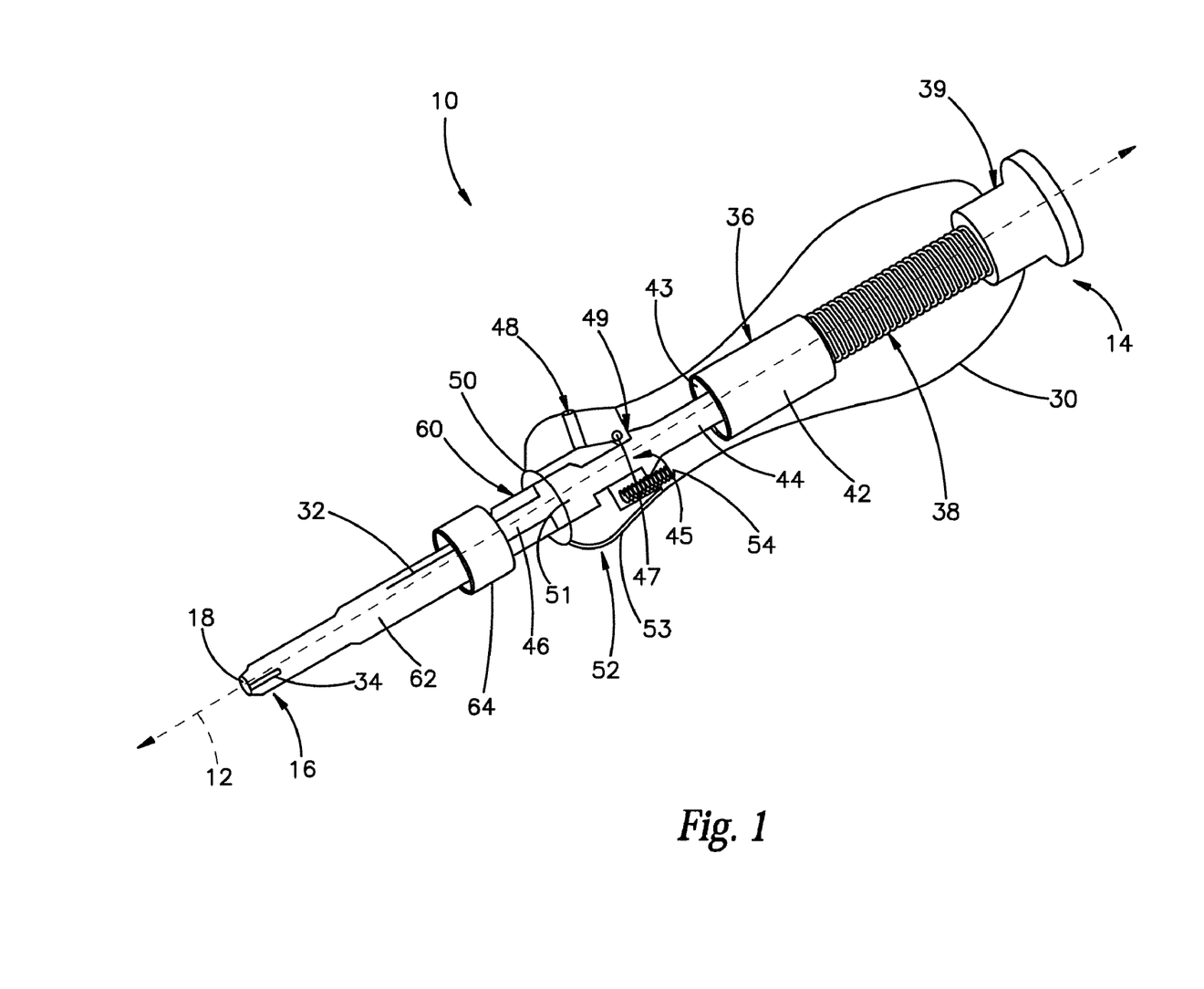
FIG. 1 is a partially transparent elevated view of one embodiment of an insertion device according to the present invention.

Referring to FIG. 1, a preferred fixation element insertion device 10 according to the present invention generally includes a longitudinal member extending along a longitudinal axis 12 from a proximal end 14 to a distal end 16 and having a channel 18 extending therein. The insertion device is preferably used to drive an osteosynthetic fixation element, such as a resorbable tack, into bone tissue. Channel 18 is configured and dimensioned to receive at least one fixation element for storage, transport, dispensing, and/or insertion into bone.

Figure 2:
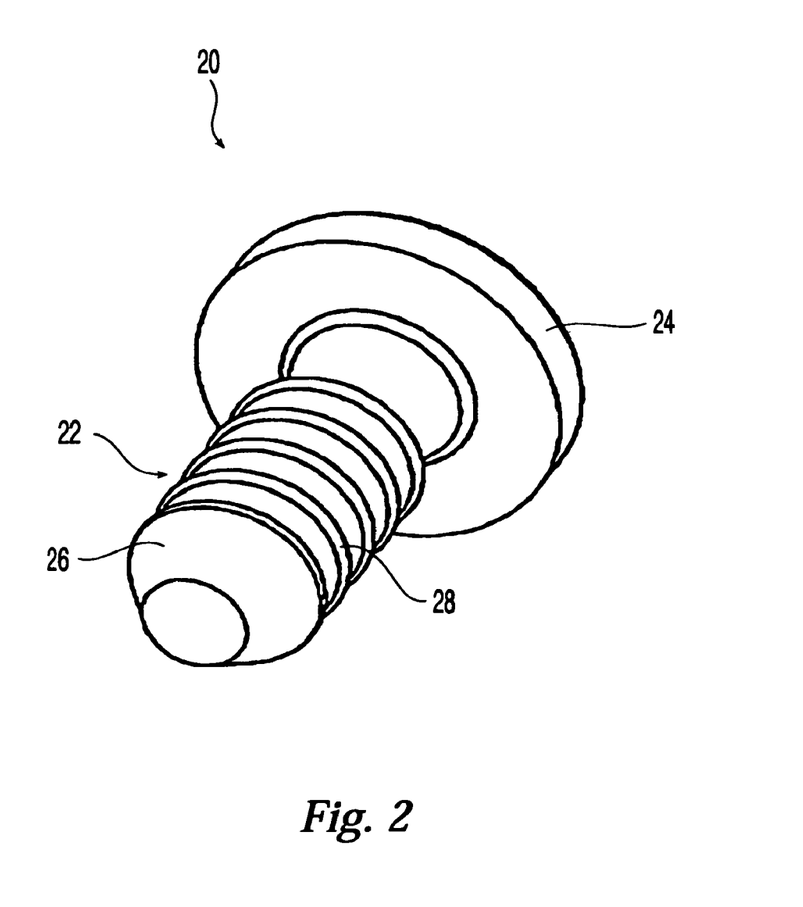
FIG. 2 is an elevated view of a fixation element for use with the insertion device of FIG. 1.

Referring to FIG. 2, one preferred fixation element compatible with insertion device 10 comprises a tack 20 having a shaft 22 integral with a head 24 at a proximal end thereof. The distal end of shaft 22 has a conical nose 26 to facilitate the insertion of tack 20 into bone tissue. A plurality of circular ribs 28 extend radially from the exterior of shaft 22 to prevent the removal of the tack from the bone tissue after it has been inserted. Head 24 has an outer diameter greater than the diameter of shaft 22 and contacts or rests against the bone or bone plate when the tack is inserted into bone tissue. In the preferred embodiment, the tack is made from a resorbable material so that it remains in the bone tissue temporarily and is absorbed by the body. In alternate embodiments, tack 20 can have numerously different configurations and dimensions. Also, different types of fixation elements altogether can be used with insertion device 10. For example, biocompatible screws, nails, anchors, rivets, or other similar implants can also be inserted using insertion device 10.

Figure 3:
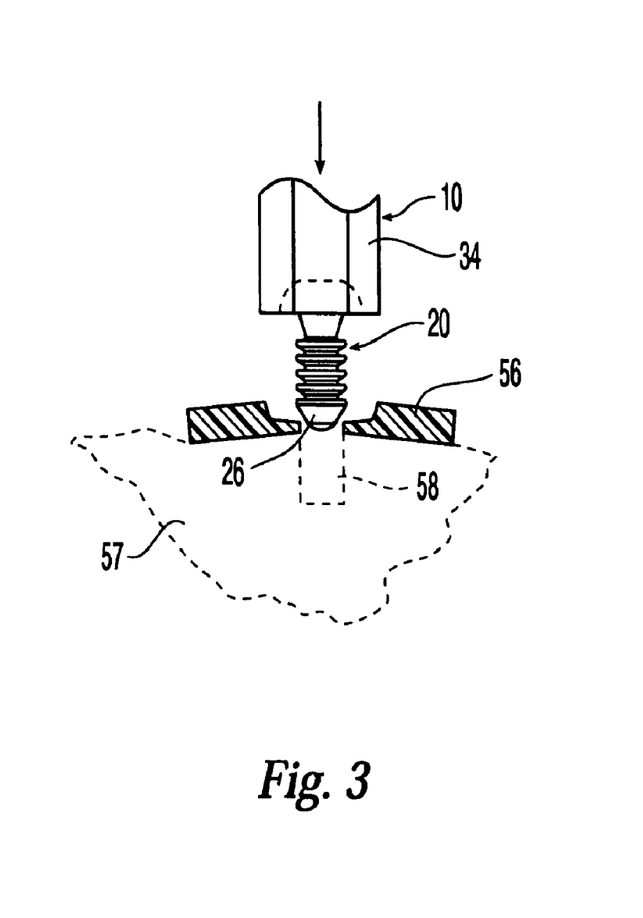
FIGS. 3-4 illustrate the placement of a fixation element within a pre-drilled hole in bone.

Referring again to FIG. 1, insertion device 10 has a handle 30 at the proximal end that is configured to conform to the shape of a person's hand or palm for easily gripping the device and an applicator extension 32 for holding and dispensing the fixation element. A central channel 18 extends within handle 30 and through extension 32 and is in communication with channel 18 at distal end 16. Channel 18 generally comprises a socket defined at the distal end 16 and an elongate applicator extension 32 extends between distal end 16 and handle 30. Extension 32 can be a unitary extension or can include multiple parts. Socket or channel 18 fits about the proximal end of fixation element 20 to hold element 20 in insertion device 10 by an interference or friction fit. In the embodiment of FIG. 1, an individual tack 20 can be held at distal end 16 and head 24 of tack 20 is preferably held within the socket or channel 18 while the shaft 22 of tack 20 projects outside thereof, as shown in FIG. 3. At the distal end of extension 32 is a pronged tip 34 for retaining a fixation element. Pronged tip 34 is generally flexible and when the distal end of extension 32 is pressed, the prongs 34 of sleeve 62 flex around the head of a fixation element to pick up and retain the element. In this way, it is possible to pick up a relatively small fixation element in a simple, single action.

A shaft member 36 and a firing spring 38 are housed within the handle 30. Shaft member 36 extends longitudinally within handle 30 and extension 32 and is preferably moveable along axis 12 with respect to handle 30 and extension 32. Firing spring 38 is positioned at the proximal end of handle 30 and is compressible between a force adjustment dial 39 at proximal end 14 and a proximal end of shaft member 36, biasing shaft member 36 in a distal direction. Shaft 36 is generally cylindrical and includes a base portion 42 that slidingly engages the interior of channel 18 within handle 30, a mid-section 44 having a smaller diameter than base portion 42, and a tip portion 46 having a smaller diameter than mid-section 44. A first shoulder 43 is positioned at the transition of base portion 42 and mid-section 44 and a second shoulder 45 is positioned at the transition of mid-section 44 and tip portion 46.

Shaft 36 is moveable from a loaded position (shown in FIG. 1) to an unloaded position for inserting a fixation element into bone. An activation button 48 extends within channel 18 for activating the movement of shaft 36 from a loaded position to an unloaded position. Button 48 is positioned along a portion of handle 30 and partially extends within channel 18 for engaging shaft 36. Referring to FIG. 1, when shaft 36 is in the loaded position ledge 49 at the proximal end of button 48 engages second shoulder 45 preventing shaft 36 from moving in the distal direction or to the unloaded position. When button 48 is depressed by an operator, ledge 49 is moved out of engagement with shoulder 45, thereby permitting shaft 36 to move in the distal direction under the force exerted by firing spring 38 on shaft 36. As a result, tip portion 46 of shaft 36 is advanced in the distal direction to force fixation element out of extension 32 and shaft 36 is moved to an unloaded position.

In a preferred embodiment, button 48 is pivotably positioned about a pin 47 and the distal portion of button 48 is biased radially outward by a spring 50 so that ledge 49 at the proximal portion of button 48 is biased inward toward engagement with shoulder 45. In this regard, a collar 51 is preferably positioned within handle 30 for engaging spring 50 in the radial direction and permitting mid-section 44 of shaft 36 to slide therethrough without engaging spring 50. When button 48 is depressed, ledge 49 is pivoted radially outward and out of engagement with shoulder. In alternate embodiments, different button assemblies or triggering mechanisms can be used.

In a preferred embodiment, a thumb slide 52 is positioned along a portion of handle 30 opposite activation button 48 and is moveable in the longitudinal direction for moving shaft 36 from an unloaded to a loaded position. Thumb slide 52 partially extends within channel 18 for engaging shaft 36 and moving shaft 36 in the longitudinal direction. In an unloaded position, shoulder 45 engages an inner ledge 53 of thumb slide 52 and when thumb slide 52 is moved in the proximal direction by an operator, shaft 36 is also retracted. To move shaft 36 to the loaded position, thumb slide 52 is moved in the proximal direction until shoulder 45 slides beyond ledge 49 of button 48 and ledge 49 engages shoulder 45, thereby locking shaft 36 in the loaded position. This shaft retraction will also compress firing spring 38. In a preferred embodiment, a spring 54 is housed within handle 30 and biases thumb slide 52 in the distal direction and once shaft 36 is in the loaded position, the thumb slide is released and returns to its resting position. Once shaft 36 is again in the loaded position, another tack can be inserted into the extension 32.

Figure 4:
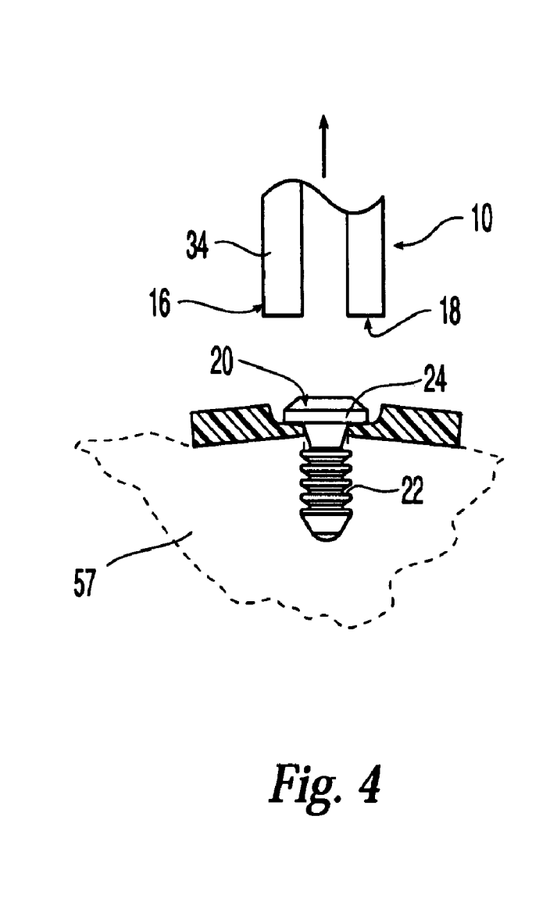

Referring to FIGS. 3-4, once the insertion device is loaded, the insertion device can be used to fasten a plate 56 or other device to a bone 57. In operation, a hole 58 is pre-drilled in the bone tissue at the desired insertion location and the insertion device 10 is placed adjacent the insertion location and the tack is aligned with hole 58. The activation button 48 is depressed to release shaft 36, and shaft 36 is driven in the distal direction by the force of firing spring 38 thereby driving tack 20 into the bone tissue. As shown in FIG. 4, once tack 20 is inserted into bone, insertion device 10 is withdrawn from the insertion location and tack 20 is separated from channel 18. When the insertion device 10 is withdrawn, the forces holding shaft 22 of tack 20 to bone 57 are greater than the forces of the interference fit between head 24 and channel 18 so that head 24 of tack 20 is separated from distal end 16, leaving tack 20 secured to the bone. The device 10 can then be reloaded by moving the thumb slide in the proximal direction as explained above and inserting another tack into extension 32. The steps are then repeated for each tack until the plate 56 is adequately secured. Advantageously, the thumb slide and activation button configuration of device 10, permits a surgeon to cock and fire, or load and unload the device using only one hand. It also noteworthy that no external parts of device 10 move during the firing or unloading movement of the device which desirably minimizes the chances that a surgeon's hand is pinched or a glove is torn. Also, in a preferred embodiment, insertion device 10 is constructed from stainless steel and anodized aluminum and as a result is a reusable device and autoclavable between uses.

Referring again to FIG. 1, extension applicator 32, preferably comprises a stem 60 with a holding sleeve 62 removably attached thereto by a coupling member 64. Holding sleeve 62 can be removed and replaced with various sized holding sleeves to accommodate tacks of differing shapes and sizes.

In a preferred embodiment, holding sleeve 62 can be easily removed without the need for tools or hardware.

Referring again to FIG. 1, preferably a force adjustment dial 39 is positioned at proximal end 14 of the device 10 and threadably engages handle 30. Dial 39 can be rotated and moved in the proximal and distal direction with respect to handle 30 for varying the amount of compression of firing spring 38 and thereby adjusting the amount of force exerted upon shaft 36 and overall force of insertion of tack 20. Also in another embodiment shown in FIG. 6, a force adjustment gauge 66 can be inserted in handle 30 for delineating the amount of force applied. For example, a line on a force adjustment gauge can show the relative position between minimum and maximum force settings and be visible through a cutaway in the handle. This feature desirably allows a surgeon to gauge the level of insertion force and adjust according to bone quality and surgeon preference.

Figures 5, 6:
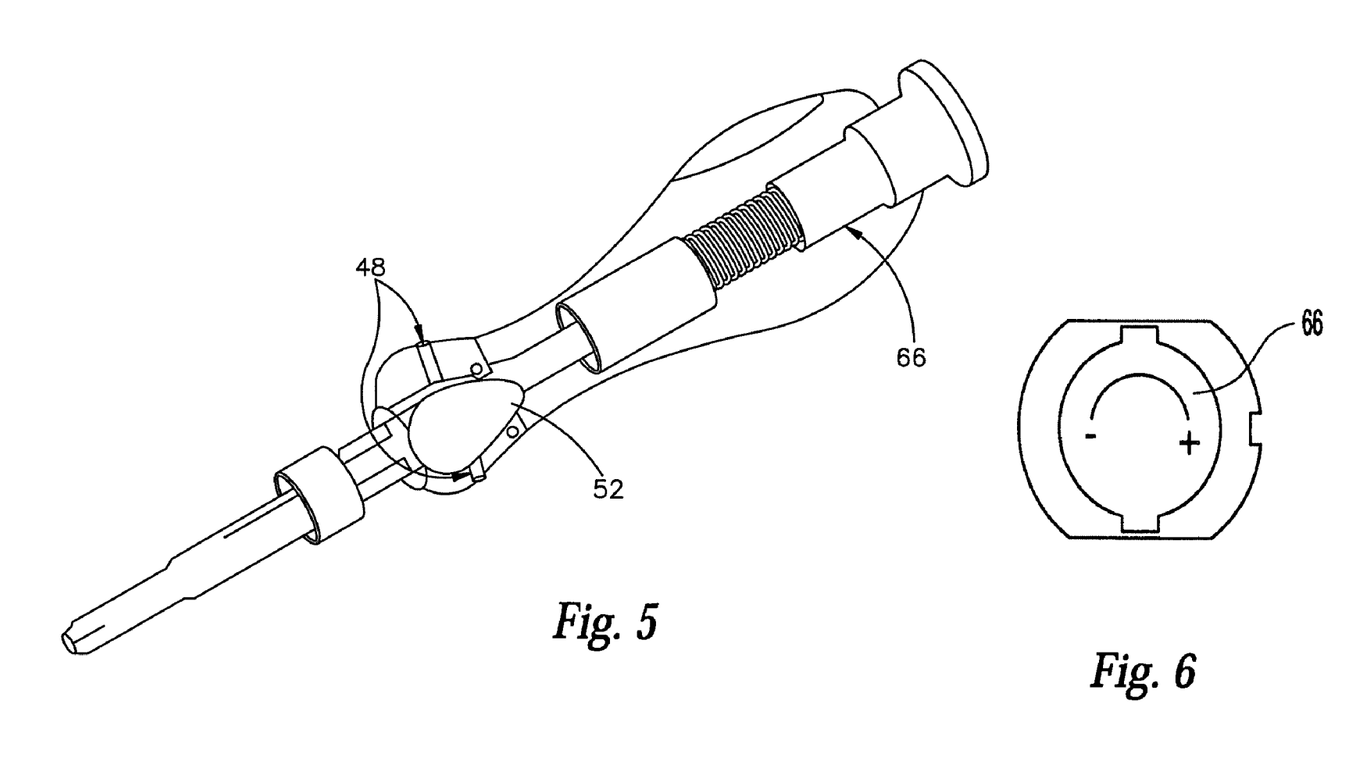
FIG. 5 is a partially transparent elevated view of another embodiment of an insertion device.
FIG. 6 is a partial elevated view of the device of FIG. 5.

Referring to FIG. 5, in an alternate embodiment, a pair of activation buttons 48 can be used instead of a single button. In this embodiment, both buttons must be depressed in order to release shaft 36, thereby providing a safety feature so that a tack is not accidentally fired. As seen in FIG. 5, activation buttons 48 are positioned on opposite sides of handle 30 and are offset 90° with respect to thumb slide 52. Of course, other safety features can also be incorporated into device 10 to prevent accidental firing.

Figure 7:
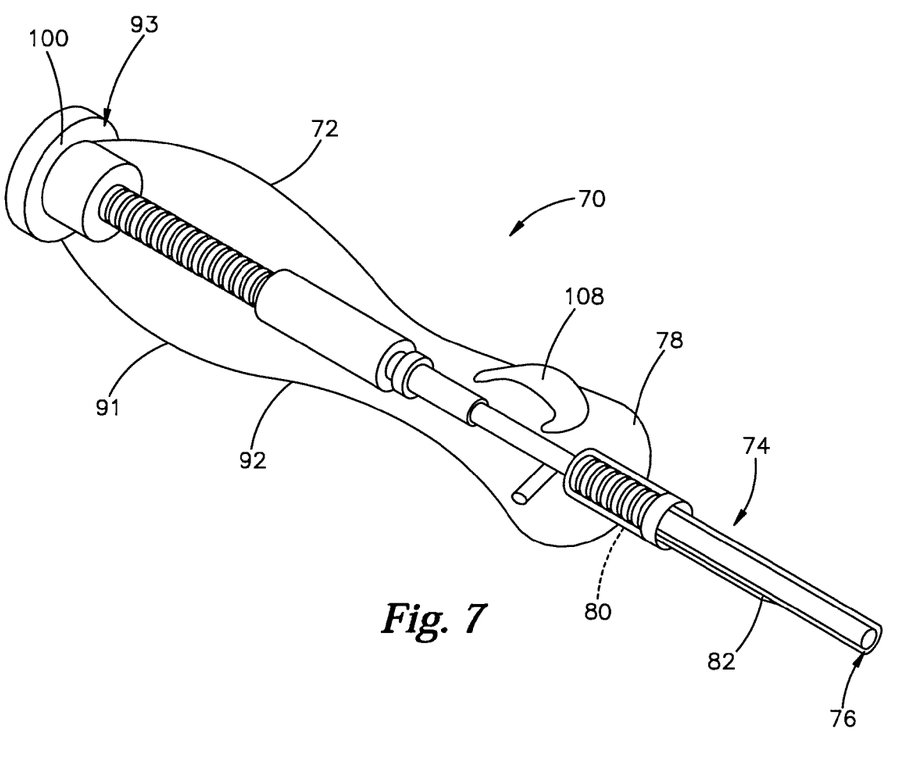
FIG. 7 is a partially transparent elevated view of another embodiment of an insertion device.
Figure 8:
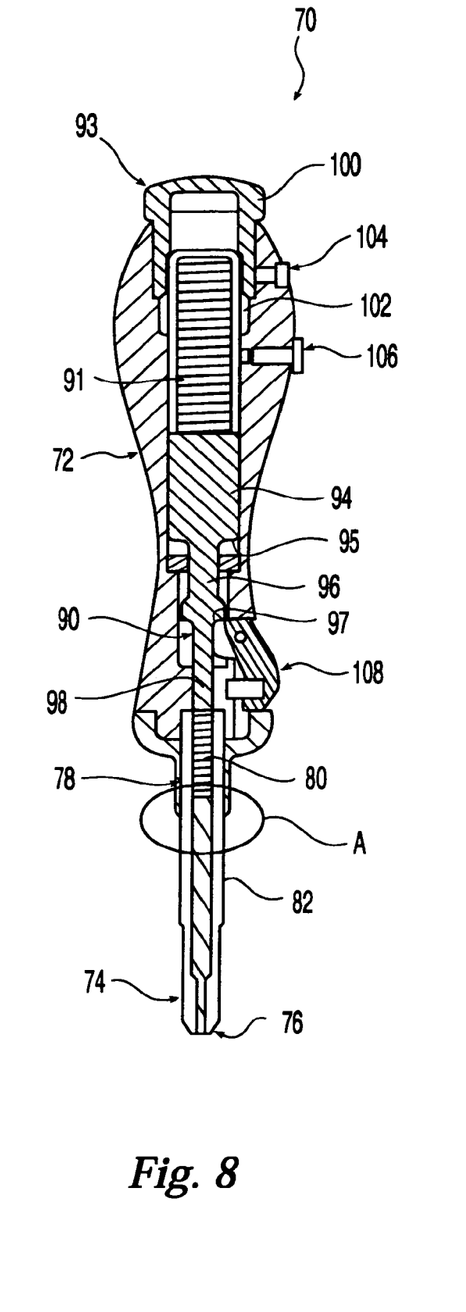
FIG. 8 a cross-sectional view of the embodiment of FIG. 7.
Figure 9:
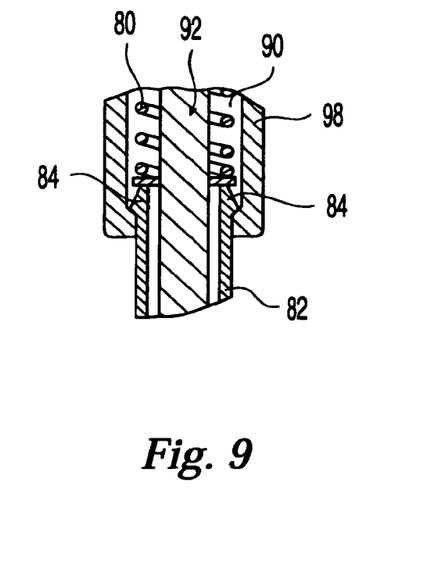
FIG. 9 is a partial cross-sectional view of a portion A of the device of FIG. 8.

Referring to FIGS. 7-9, an alternate embodiment of an insertion device 70 is shown that has an alternative loading mechanism. Insertion device 70 includes a handle 72 at a proximal end and a spring loaded elongate applicator extension 74 extending between distal end 76 and handle 72. Extension 74 comprises a spring cover 78 attached to handle 72 for housing spring 80 and a holding sleeve 82 coaxially attached to the distal end of spring cover 78 in a telescoping fashion for receiving a fixation element. Sleeve 82 has slightly smaller external dimensions than the internal dimensions of cover 78 so that the proximal end of sleeve 82 can be inserted into the distal end of cover 78 and sleeve 82 can move in the axial direction with respect to cover 78. As best seen in FIG. 9, sleeve 82 can include prongs that interlock with ridges on the interior of cover 78 so that when sleeve 82 is inserted into cover 78, sleeve 82 is not inadvertently removed from cover 78 in the distal direction. In a preferred embodiment, sleeve 82 has prongs 84 that are flexible and are collapsible or bendable into the interior of sleeve 82 so that sleeve 82 can be removed from cover 78 for cleaning, disassembly, or replacement. Prongs 84 are biased radially outwardly so that sleeve 82 can be easily reattached by simply pushing the sleeve into the cover in the proximal direction. The distal end of sleeve 82 preferably has a pronged tip similar to that described previously for retaining a fixation element.

A central channel 90 extends within handle 72 and through extension 74 and houses a firing spring 91 and a shaft member 92 similar to the embodiment of FIG. 1. Firing spring 91 is biased between force adjustment dial 93 and the proximal end of shaft 92. Adjustment dial 93 includes a knob 100 with internal threading that engages an externally threaded adjustment slider 102 that is slidably housed within channel 90. When knob 100 is rotated, adjustment slider 102 slidably moves within channel 90 and compresses or decompresses spring 91 for adjusting the amount of force that is exerted on shaft 92 and consequently the tack during insertion. A pair of knob retaining screws 104 extend radially inward from the exterior of handle 72 and engage a circular groove in knob 100 for retaining knob 100 in the proximal end of handle 72.

A guide screw 106 extends inward from handle 72 and engage a longitudinal groove in adjustment slider 102 to prevent the slider from rotating.

Shaft 92 extends longitudinally within handle 72 and is generally identical to shaft 36 described above, moving between a loaded and an unloaded position. Shaft 92 includes a base portion 94, a mid-section 96 having a smaller diameter than base portion 94, and a tip portion 98 having a smaller diameter than mid-section 96. A first shoulder 95 is positioned at the transition of base portion 94 and mid-section 96 and a second shoulder 97 is positioned at the transition of mid-section 96 and tip portion 98. Device 70 includes an activation button 108 similar to button 48 described above for facilitating movement of shaft 92 from the loaded to the unloaded position in the same fashion as described with respect to the embodiment of FIG. 1. To move shaft 92 from the unloaded to the loaded position, holding sleeve 82 and tip portion 98 of shaft 92 is retracted in the proximal direction until shoulder 97 of shaft 92 slides beyond button 108 and the button engages shoulder 97, thereby locking shaft 92 in the loaded position in a similar fashion to button 48 described above. Also, insertion device 70 preferably has a spring 80 housed within spring cover 78 that biases holding sleeve 82 in the distal direction and once shaft 92 is in the loaded position, the holding sleeve is released and returns to its resting position. In this way, shaft 92 can be easily moved from the unloaded to the loaded position, by depressing device 70 in the distal direction against a solid object, such as a table or a surgeons hand. In all other respects, the method of operation or use of device 70 is similar to the method described above with respect to device 10.

Figure 10:
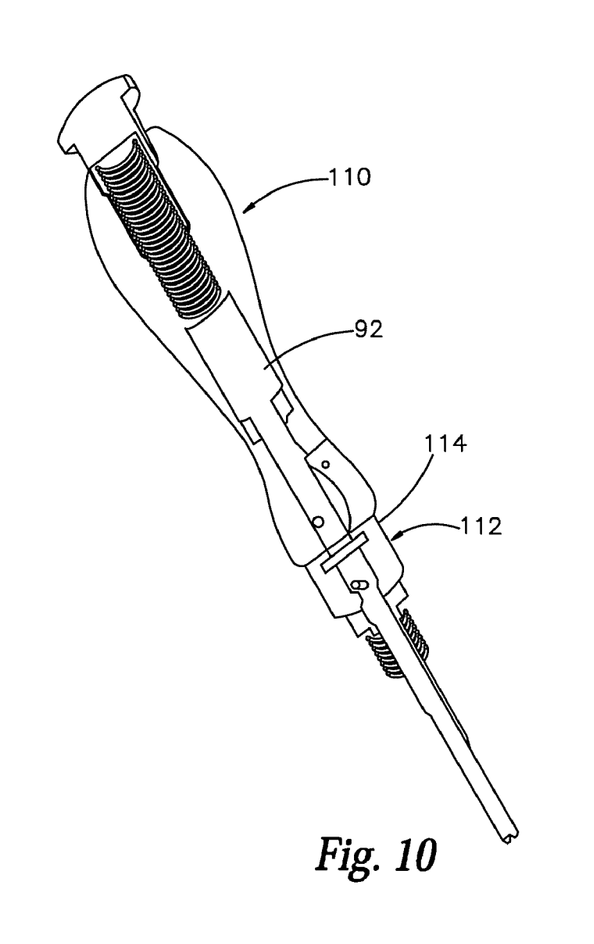
FIG. 10 is an elevated view of another embodiment of an insertion device.
Figure 11:
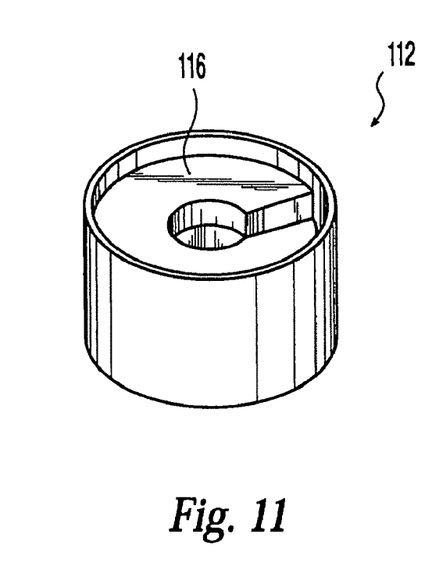
FIG. 11 is an elevated view of a cam member of the device of FIG. 10.

Referring to FIGS. 10-11, another embodiment of an insertion device 110 is shown that has yet another alternative loading mechanism. In all other respects, device 110 is similar to device 70 described previously. Insertion device 110 has a cam 112 for moving shaft 92 from the unloaded to the loaded position. In this embodiment, shaft 92 has pins 114 extending outwardly therefrom that engage an internal ramp 116 within cam 112 and when cam 112 is rotated pins 114 slide along ramp 116 in the proximal direction and thereby move shaft 92 in the proximal direction and shaft 92 is retracted until shoulder 97 of shaft 92 slides beyond button 108 and the button engages shoulder 97, thereby locking shaft 92 in the loaded position in a similar fashion to button 48 described above. After shaft 92 is locked into the loaded position, cam 112 is rotated to provide clearance for pins 114 to move in the distal direction during the unloading or firing movement of shaft 92.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A device for attaching a fixation element to bone, the device defining a proximal end and an opposing distal end, the device comprising:

a handle having a proximal portion and a distal portion, the handle having an internal channel;

a spring cover attached to the handle, the spring cover having a central opening in communication with the internal channel of the handle;

a holding sleeve having a proximal portion and a distal portion, the holding sleeve distal portion located distal to the distal portion of the handle and adapted to retain at least a proximal portion of a fixation element, wherein the holding sleeve designed to telescopically travel within the central opening of the spring cover, and the distal portion of the holding sleeve defines a distal contact surface;

a shaft member having a proximal end located within the internal channel of the handle and a distal end located outside of the internal channel of the handle, the shaft member having a distal tip at the distal end located within the holding sleeve, the shaft member having a shoulder within the internal channel of the handle;

a firing spring positioned within the internal channel of the handle and adjacent the proximal end of the shaft member for resiliently biasing the shaft member in a distal axial direction;

a firing button located on the distal portion of the handle, the button having a ledge located on its proximal end for engaging the shoulder of the shaft member when the firing spring is in a loaded position; and a distal spring located within the spring cover and distal to the firing button, wherein the distal spring biases the holding sleeve distally;

wherein applying a proximally directed force against the distal contact surface of the holding sleeve causes the shaft to move to the firing spring to the loaded position.

2. The device of claim 1, wherein the firing button is pivotally mounted to the handle and is resiliently biased into the loaded position.

3. The device of claim 1, further comprising an adjustment gauge located on the proximal end of the handle for adjusting the bias of the spring.

4. The device of claim 1, wherein the holding sleeve comprises flexible and bendable prongs located in the proximal portion of the holding sleeve wherein the prongs are designed so that the holding sleeve can be removed from the spring cover.

5. The device of claim 1, wherein the holding sleeve comprises at least one flexible prong that is moveable in a radially inward direction and biased in a radially outward direction so as to place the holding sleeve in removable engagement with the distal end of the spring cover.

6. The device of claim 1, wherein the distal portion of the holding sleeve receives the fixation element.

7. The device of claim 1, wherein the distal contact surface of the holding sleeve defines the distal end of the device.

8. The device of claim 1, wherein the proximally directed force is applied directly against the distal contact surface of the holding sleeve.

9. A device for attaching a fixation element to bone, the device defining a proximal end and an opposing distal end, the device comprising:

a handle having a proximal portion and a distal portion, the handle having an internal channel;

a spring cover attached to the handle, the spring cover having a central opening in communication with the internal channel of the handle;

a holding sleeve having a proximal portion and a distal portion, the holding sleeve distal portion located distal to the distal portion of the handle and adapted to retain at least a proximal portion of a fixation element, wherein the holding sleeve designed to telescopically travel within the central opening of the spring cover;

a shaft member having a proximal end located within the internal channel of the handle and a distal end located outside of the internal channel of the handle, the shaft member having a distal tip at the distal end located within the holding sleeve, the shaft member having a shoulder within the internal channel of the handle;

a firing spring positioned within the internal channel of the handle and adjacent the proximal end of the shaft member for resiliently biasing the shaft member in a distal axial direction;

a firing button located on the distal portion of the handle, the button having a ledge located on its proximal end for engaging the shoulder of the shaft member when the firing spring is in a loaded position; and a distal spring located within the spring cover and distal to the firing button, wherein the distal spring biases the holding sleeve distally;

wherein pushing the distal portion of the holding sleeve proximally causes the shaft to move to the firing spring to the loaded position.

10. The device of claim 9, wherein the firing button is pivotally mounted to the handle and is resiliently biased into the loaded position.

11. The device of claim 9, further comprising an adjustment gauge located on the proximal end of the handle for adjusting the bias of the spring.

12. The device of claim 9, wherein the holding sleeve comprises flexible and bendable prongs located in the proximal portion of the holding sleeve wherein the prongs are designed so that the holding sleeve can be removed from the spring cover.

13. The device of claim 9, wherein the holding sleeve comprises at least one flexible prong that is moveable in a radially inward direction and biased in a radially outward direction so as to place the holding sleeve in removable engagement with the distal end of the spring cover.

14. The device of claim 9, wherein the distal portion of the holding sleeve a receives the fixation element.

* * * * *

UNITED STATES PATENT AND TRADEMARK OFFICE
CERTIFICATE OF CORRECTION

PATENT NO. : 8,052,691 B2  Page 1 of 1
APPLICATION NO. : 10/992259
DATED : November 8, 2011
INVENTOR(S) : Ralph Fritz Zwirnmann et al.

It is certified that error appears in the above-identified patent and that said Letters Patent is hereby corrected as shown below:

On the Title Page, please insert item 63:

-- Related U.S. Application Data

Continuation of U.S. Application No. 10/287,693, filed on Nov. 5, 2002, now abandoned; which claims priority to Provisional Application No. 60/330,977, filed on Nov. 5, 2001; and which claims priority to U.S. Application No. 09/866,841, filed on May 30, 2001, now U.S. Pat. No. 7,147,641 and PCT International Application No. PCT/US02/16656, filed on May 28, 2002. --

Signed and Sealed this
Twentieth Day of March, 2012

David J. Kappos
*Director of the United States Patent and Trademark Office*